(12) United States Patent
Wang et al.

(10) Patent No.: US 7,238,322 B2
(45) Date of Patent: Jul. 3, 2007

(54) DELAYED AND DIFFUSED FLOW RAPID CONFIRMATORY IMMUNOLOGICAL TESTING APPARATUS AND METHOD

(75) Inventors: Naishu Wang, San Diego, CA (US); David F. Zhou, San Diego, CA (US)

(73) Assignee: DNT Scientific Research, LLC, San Diego, CA (US)

( * ) Notice: Subject to any disclaimer, the term of this patent is extended or adjusted under 35 U.S.C. 154(b) by 0 days.

(21) Appl. No.: 11/258,636

(22) Filed: Oct. 26, 2005

(65) Prior Publication Data
US 2006/0051237 A1 Mar. 9, 2006

Related U.S. Application Data

(63) Continuation-in-part of application No. 11/090,463, filed on Mar. 25, 2005, which is a continuation-in-part of application No. 10/767,897, filed on Jan. 28, 2004.

(51) Int. Cl.
*G01N 21/00* (2006.01)
*G01N 15/06* (2006.01)
*G01N 33/53* (2006.01)
*B01L 3/00* (2006.01)
*B01L 11/00* (2006.01)
*B32B 5/02* (2006.01)
*C12Q 1/00* (2006.01)
*C12M 1/36* (2006.01)
*C12M 3/00* (2006.01)
*C12M 1/34* (2006.01)

(52) U.S. Cl. .......................... 422/58; 422/61; 422/68.1; 422/101; 422/102; 435/4; 435/7.1; 435/286.4; 435/286.5; 435/286.7; 435/287.1; 435/287.2; 435/287.3; 435/287.6; 435/287.7; 435/288.5; 435/288.7

(58) Field of Classification Search .................. 422/58, 422/61, 68.1, 101, 102; 435/4, 7.1, 286.4, 435/286.5, 286.7, 287.1, 287.2, 287.3, 287.6, 435/287.7, 288.5, 288.7
See application file for complete search history.

(56) References Cited

U.S. PATENT DOCUMENTS 6,248,294 B1 * 6/2001 Nason .......................... 422/58

(Continued)

*Primary Examiner*—Long V. Le
*Assistant Examiner*—Jacqueline A. DiRamio
(74) *Attorney, Agent, or Firm*—Charmasson, Buchaca & Leach, LLP (57) ABSTRACT

A self-contained apparatus using a gravitationally encouraged, interrupted, downward, diffusive and programmed flow of fluid to provide for rapid confirmatory immunological testing ("RCIT") in, for example, a clinical, point-of-care setting. A fluid specimen such as blood, saliva or urine is deposited into a first chamber carrying a source of conjugate having mobilizable binding members such as immunographic antigens or antibodies specific to the condition being tested conjugated to a detectable label such as colloidal gold. The specimen is premixed with a first measured, reactive mix buffer solution carried within an openable tank. The specimen and solution are temporarily held within an incubation reservoir formed behind a dam made from porous, diffusive material. The delay and flow through the diffusive dam causes mixing of the specimen and solution to form a premixture which exhibits a more uniformly high degree of first affinity binding before flowing out of the first chamber toward one or more chromatographic test strips in a second chamber. In one embodiment, after a waiting period, a bladder containing a stop-wash buffer solution is opened to flow onto the strips. Additional embodiments provide one or more diffusive structures that can be pretreated with mixture enhancing chemicals such as surfactants. It is a rapid confirmatory immunological test apparatus having an analytical panel which can provide profile diagnostic results.

21 Claims, 7 Drawing Sheets

U.S. PATENT DOCUMENTS

| | | | |
|---|---|---|---|
| 6,300,142 B1* | 10/2001 | Andrewes et al. | 436/518 |
| 6,663,833 B1* | 12/2003 | Stave et al. | 422/81 |
| 6,890,484 B2* | 5/2005 | Bautista et al. | 422/58 |
| 2002/0086436 A1* | 7/2002 | Buechler | 436/164 |
| 2003/0017467 A1* | 1/2003 | Hooper et al. | 435/6 |
| 2003/0077616 A1* | 4/2003 | Lomas | 435/6 |
| 2003/0186456 A1* | 10/2003 | Stroup | 436/165 |
| 2004/0053422 A1* | 3/2004 | Chan et al. | 436/180 |
| 2005/0112023 A1* | 5/2005 | Liang | 422/58 |
| 2005/0164404 A1* | 7/2005 | Marlborugh et al. | 436/514 |
| 2005/0164406 A1* | 7/2005 | Carroll et al. | 436/514 |

\* cited by examiner

FIG. 20 though these prior devices provide a convenient, quick, economic, and simplified way to conduct such testing without requiring sophisticated instrumentation or

DELAYED AND DIFFUSED FLOW RAPID CONFIRMATORY IMMUNOLOGICAL TESTING APPARATUS AND METHOD

PRIOR APPLICATION

This is a continuation-in-part of co-pending U.S. patent application Ser. No. 11/090,463 filed Mar. 25, 2005 which is a continuation-in-part of U.S. patent application Ser. No. 10/767,897 filed Jan. 28, 2004.

FIELD OF THE INVENTION

This invention relates to rapid confirmatory testing apparatuses for analyzing body fluids and other fluids using immunochromatography, and more particularly to fluid test apparatuses for detecting antibodies or antigens in a near-patient setting, such as at the point-of-care, and/or in a clinical laboratory setting conducting large scale rapid, confirmatory examination.

BACKGROUND

Over past decades, the prior art has offered several types of rapid diagnostic testing techniques primarily for body fluids such as whole blood, serum, plasma, urine, spinal fluid, amniotic fluid, mucous, saliva, and the like for the presence of infection or other conditions such as pregnancy, abused drugs and cardiovascular disorders such as acute myocardial infarction (AMI).

The first of these tests were the Latex Particle Agglutination tests, then the Flow Through tests leading to the current Lateral Flow Single Step test. Such tests typically utilize well known sandwich-type immunoassay techniques. In such tests a fluid specimen is supplied from a subject which could carry at least one analyte, such as an antibody, which is specific to the condition being tested. The fluid specimen is exposed to a conjugate having at least one mobilizable binding member, such as an antigen (or antibody in some cases), which has immuno-determinant(s) (or specific binding sites for the immuno-determinant(s) in certain cases) of the analyte in question. The binding member is conjugated to a visibly detectable label such as colloidal gold. During exposure of the specimen to the conjugate, an immuno-chemical reaction occurs wherein the analyte in question binds to the binding member to form the first affinity binding labeled analyte complex.

The fluid containing the labeled analyte complex is then directed to flow into a reaction membrane having a zone coated with at least one immobilized capture binding member which is similarly immuno-determinant of the analyte in question. As the fluid passes through the membrane, a second immuno-chemical reaction occurs wherein the labeled analyte complex binds to the capture binding member to form the second affinity binding immuno-sandwich complex. The accumulation of the secondly bound immuno-sandwich complex beyond a threshold amount in the zone creates a colored test line, the so-called "T-line". The reaction membrane typically has a second zone located further downstream from the T-line as an internal system control line, the so-called "C-line". The control line is used as an internal indicator of functional validity.

Unfortunately, depending on the type of condition being detected, these tests provide a typical accuracy of between 85% and 99%, falling short of the 99.5% or above accuracy generally considered to be necessary for a confirmatory test.

The reasons for the insufficient accuracy are primarily due to the lack of overall higher sensitivity and specificity of the apparatus. Different samples may contain chemicals or particles which interfere with or inhibit the fluid flow or otherwise interfere with one or both of the affinity binding reactions. Prior apparatuses have attempted to enhance sensitivity or specificity by pretreating various parts of the apparatus with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially on the reaction membrane. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Or, the manufacturing step of pretreating with the second pretreatment chemical can dislodge some of the first pretreatment chemical.

Further, lot-to-lot variation in the manufacture of the test apparatuses can often lead to ambiguous results, such as false negatives as well as weak false positives, so-called "ghost lines" or "phantom lines". False negatives typically occur when non-specific molecules interfere with the first and/or second affinity binding actions. It has been found that non-analyte molecules can clump together in fluid samples that are not well mixed so that they temporarily prevent access between analytes and binding members. Even temporary interference can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive.

Chemically non-uniform flows can result in flows having non-uniform first affinity binding by the time they reach the reaction membrane leading to inaccuracies. Such non-uniform flows can be caused by a number of factors. First, some portions of the fluid may flow faster than others from time to time. In those tests having deposits of dried reagent, faster flows tend to reach the dried reagent first. These flows tend to exhibit a greater degree of first affinity binding per unit fluid or at least uptake of mobilizable labeled binding members, and can potentially carry a greater concentration of clumps of non-analyte molecules which can carry away labeled mobilized binding members. Further, the deposit of dried reagent itself can exhibit portions of higher concentration than others resulting in similar chemical nonuniformity in the flow. Other flows having a lower than average concentration of analyte molecules, and/or having a greater concentration of non-clumped, non-analyte molecules which merely inhibit analyte binding but do not carry away mobilizable labeled binding members, exhibit less apparent first affinity binding. These flow and concentration disuniformities are responsible for many of the unsatisfactory results discussed above.

Therefore, although these prior devices provide a convenient, quick, economic, and simplified way to conduct such testing without requiring sophisticated instrumentation or trained professionals, in many settings these rapid tests are useful only for preliminary screening purposes, not as a confirmatory test. To this day, for example, the Western Blot Analytical Assay is the only one reliably used for the confirmatory detection of HIV infection in a clinical laboratory setting worldwide. Due to its multi-step manipulation and verification phases, completion of this type of assay takes days, if not weeks. Such a delay can unfortunately lead to further propagation of infectious pathogens such as HIV or other serious results, such as the metastasis of cancers. There is virtually no generally accepted practical or economical confirmatory rapid diagnostic testing technique for use in a point-of-care setting to rapidly detect serious diseases such as HIV infection and AMI, available in the market place today.

Therefore, there is a need to refine the accuracy and expedite the performance of prior immunoassay chromatographic rapid testing apparatuses to a higher and new level for use in the speedy and early detection and confirmation of the presence of pathogens or pathogenic conditions such as occurs with HIV infection, cancers and other disorders.

SUMMARY

The instant embodiments provide an apparatus capable of rapidly conducting a confirmatory immunoassay test for an analyte (or analytes) in question. These instant embodiments may also provide an apparatus that can be used, for example, in a point-of-care setting.

In one embodiment there is provided a self-contained, multi-stage, programmed, interrupted downward flow, rapid confirmatory immunological test ("RCIT") apparatus contained in a single molded enclosure. The immunoassay test can be performed in either a sandwich and/or competitive assay format. The apparatus can carry one or more chromatographic test strips in an inclined downward orientation forming "down-flow" test strips. The primary exposure of a fluid specimen to a specific antibody or antigen (or to a group thereof) conjugated to a label such as colloidal gold, or other type of label such as colloidal carbon, latex beads, or magnetic beads, etc. (hereinafter "conjugate") in a volume measured, reactive, buffered solution occurs in a first premix chamber before flowing on to contact the strips in a second chamber. A holding reservoir located on a fluid path between the first and second chambers interrupts the flow of the mixture to allow a short period of mixing incubation before proceeding with the secondary specific immunological binding reaction in the reaction membranes of the strips. The incubation period allows for further mixing of the fluid resulting in a greater degree of proper first affinity binding compared to prior rapid test technology.

In some embodiments, the down-flow strips are not of the type used by prior lateral flow testing methods in that they are not directly connected with any conjugate pad, but rather provide a reaction membrane which links with the outflow of the reservoir at the strip's top end. The down-flow strips can include a single layer of uniformly dispersed porous matrix material such as uniformly porous polyethylene commercially available from Porex Corporation of Fairburn, Ga.

In some embodiments, a supply of aqueous mix buffer solution is held in a sealed tank until the sample specimen has been introduced into the apparatus and its cap closed. A prong in the undersurface of the cap punctures a membrane sealing the upper opening of the tank allowing the buffer solution to be dispensed into a first chamber under atmospheric pressure. A pad at the bottom of a second chamber in contact with a lower part of at least one down-flow strip absorbs the excess wash buffer that has not been retained by the strip. The strip or strips can be held in an inclined rather than straight vertical position in order to reduce the height of the apparatus. The flow out of the incubation reservoir and into the strip is prompted by a combination of siphoning, gravity and capillarity action forces.

In still other embodiments, the enclosure is shaped to orient the test strips on an incline from horizontal. A first measured supply of aqueous mix buffer solution is held in an openable tank until the sample specimen has been introduced through an inlet into the first chamber containing a pad impregnated with an amount of lyophilized conjugate utilizing colloidal gold or other label. Under the push of a manipulable member, the tank seal is opened, causing the mix buffer to flow into and mix with the sample and conjugate. A porous dam interrupts the flow out of the first chamber to incubate the mixture. Further, the flow through the porous dam causes improved mixing of the fluid to provide a more uniformly high degree of first affinity binding. The mixed and incubated fluid then flows out of the first chamber into a second chamber containing one or more downward-flow oriented chromatographic strips.

The flow through the dam and down-flow strips is prompted by a combination of siphoning, surface tension and gravity forces. After waiting for an adequate amount of time for the mixture to flow through the strips, a second tank containing an amount of wash buffer solution is opened under the push of another manipulable member to wash down the remaining mixture through the first chamber and the strips and end the reaction at the signal zones on the strips. The lower pad absorbs the wash buffer and, along with the angled orientation of the strips, discourages reverse flow of fluid back up into the strips. Both of the manipulable members are movable, built-in components of the apparatus.

The instant apparatus has many unique and advantageous features, including a self-contained measured volume mix and wash buffer tanks, a simplified program for successively opening these tanks during processing, interrupted flow from the first chamber to the second chamber, and diffusive action of the porous dam having numerous fluid furcations and convergences that provide more uniform mixing which improves accuracy and makes the apparatus well suited to rapid diagnostic point-of-care and/or near-patient testing.

Some of the instant embodiments provide, a flow immunoassay testing apparatus for testing a fluid specimen for the presence of an analyte, said apparatus comprises: a first chamber shaped and dimensioned to accept said specimen and be subjectable to a supply of mix buffer solution and a source of labeled conjugate specific to said analyte; a second chamber holding at least one test result signal generator responsive to an amount of said analyte bonded to said labeled conjugate; and a flow-interrupting dam located on a fluid path between said first and second chambers.

In some embodiments said dam has a first porous portion. In some embodiments said first portion has a first pretreatment condition. In some embodiments said first pretreatment condition is selected from the group consisting of: being pretreated with a surfactant; being pretreated with a pH conditioner, being pretreated with a non-specific adhesive blocking molecule; and, having no pretreatment. In some embodiments said surfactant comprises a non-ionic detergent. In some embodiments said dam is a first dam and said apparatus further comprises a second dam spaced a distance apart from said first dam, wherein said second dam has a second porous portion. In some embodiments said first portion has a first pretreatment condition and said second portion has a second pretreatment condition, and said first pretreatment condition is different from said second pretreatment condition. In some embodiments said first portion comprises a material having a plurality of intersecting surface structures, wherein a junction between first and second of said structures is not substantially parallel. In some embodiments said first portion comprises a material selected from the group consisting of: fiberglass, cellulose and fibrous plastic and the like. In some embodiments said generator comprises a chromatographic test strip including a zone held on a membrane in an oblique, downward flow orientation. In some embodiments said membrane comprises a plurality of test zones adapted to provide a measurable basis for a quantitative result display. In some embodiments said membrane comprises a plurality of test zones adapted to provide a measurable basis for a qualitative result display. In some embodiments said strip is formed without a source of mobilizable labeled binding members. In some embodiments said strip further comprises a diffusive pad upstream from said zone. In some embodiments said second chamber comprises a plurality of chromatographic test strips adapted to provide a measurable basis for a quantitative result display. In some embodiments said signal generator is adapted to provide a measurable basis for a quantitative result display. In some embodiments said conjugate source comprises a lyophilized amount carried on a structure within said first chamber. In some embodiments said mix buffer solution is preformulated to carry an amount of said conjugate source in suspension. In some embodiments the apparatus further comprises means for triggering a dispensing of said supply into said first chamber. In some embodiments a volume of said supply of mix buffer solution is adjusted to create a minor outflow through said dam. In some embodiments the apparatus further comprises an openable tank shaped and dimensioned to releasably hold an amount of a wash buffer, wherein said tank in an open condition is in fluid communication with said dam. In some embodiments said supply of mix buffer solution has a volume between about 200 microliters and about 300 microliters. In some embodiments the apparatus further comprises a second supply of wash buffer solution having a volume between about 2.5 milliliters and about 3 milliliters.

In some embodiments it is provided that in an immunoassay flow testing apparatus wherein a fluid specimen in a buffered solution is first contacted with a colloidal conjugate in a first part of said apparatus, then applied to a chromatographic testing strip in a second part of said apparatus, an improvement which comprises a porous, flow interrupting and diffusing dam between said first and said second parts.

In some embodiments it is provided that in an immunoassay testing apparatus wherein a specimen is contacted with a reactive solution, the resulting mixture is applied to at least one chromatographic test strip, and said strip is contacted by a wash solution, an improvement which comprises: a first built-in manipulable member for releasing said reactive solution onto said specimen; and, a second, built-in manipulable member for releasing said wash solution onto said strip.

In some embodiments there is provided a method for premixing a measured buffer solution with a fluid specimen to form a mixture for dispensing to a chromatographic test strip, said method comprises: preloading said solution within an openable tank; placing a fluid specimen in a premix chamber; opening a passageway between said tank and said premix chamber, thereby dispensing said solution onto said specimen to create a mixture of said solution and said specimen; and, flowing said mixture from said chamber to said strip; and wherein said method further comprises delaying said flowing for an incubation period. In some embodiments the method further comprises washing said strip after passage of a time period after said flowing.

In some embodiments where it is provided that in an immunoassay apparatus comprising a conjugate source adapted to carry a mobilizable binding member molecule specific to a particular analyte and a reaction membrane carrying a capture binding member molecule, an improvement comprises: a first porous interrupting, diffusive dam located on a fluid flow path between a portion of said conjugate source and a portion of said reaction membrane, thereby creating a plurality of convergent fluid paths between said conjugate source and said membrane.

In some embodiments there is provided a method for conducting a fluid flow immunoassay wherein said method comprises: diffusing a fluid mixture comprising a specimen, a mix buffer and a conjugate through a diffusive dam before said mixture reaches at least one chromatographic test strip.

DESCRIPTION OF EXEMPLARY EMBODIMENTS

The instant apparatus is useful to rapidly and confirmatorily determine the presence of analyte in a sample. The sample can include, for example, body fluids such as whole blood, serum, plasma, urine, spinal fluid, amniotic fluid, mucous, saliva, and the like.

Analyte, as used herein, refers to a compound or composition to be measured. The analyte can be any substance (antigen or ligand) for which there exists a naturally or genetically occurring specific binding member such as a binding molecule (e.g., an antibody or receptor).

Analyte also includes any antigenic substances, haptens, antibodies, and combinations thereof. The analyte can include a protein, a peptide, an amino acid, a ligand, a hormone, a steroid, a vitamin, a drug including those administered for therapeutic purposes as well as those administered for illicit purposes, a bacterium, a virus, and metabolites of or antibodies to any of the above substances. The analyte can also comprise an antigenic marker or antibody or receptor for single or multiple pathogenic conditions.

Representative analytes include steroids such as estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine, histamine, serotonin, prostaglandins such as PGE, PGF, PGA; antiasthmatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortriptyline, amitriptyline, imipramine and desipramine; as well as metabolites thereof. Additional therapeutic drugs include, for example, carbamazepine, free carbamazepine, cyclosporine, digoxin, FK778, lithium, N-acetylprocainamide, tacrolimus, free valproic acid, and the like, as well as the metabolites thereof.

Representative analytes also include drugs of abuse, and their metabolities, including amphetamines, methamphetamines, barbiturates, benzodiazepines (BZD), cannabinoids, cocaine (benzoylecgonine), opiates, phencyclidine (PCP), tricyclic antidepressants (TCA), methadone, propoxyphene (PPX), marijuana (THC), methylenedioxymethamphetamine (MDMA, or Ecstasy, or XTC), morphine, oxycodone, and bupromorphine. Representative drugs of abuse further include ethanol, heroin, hydromophone, oxymorphone, metapon, codeine, hydrocodone, dihydrocodiene, dihydrohydroxy codeinone, pholcodine, dextromethorphan, phenazocine and deonin.

Hepatic analytes include, for example, albumin bromocresol green (BCG) or purple (BCP), alkaline phosphatase, hepatitis B core antigen/antibody (anti-HBc), hepatitis B e antigen/antibody (anti-HBe), hepatitis B surface antigen/antibody (anti-HBsAg), hepatitis C virus (HCV), anti-HCV, direct bilirubin, gamma-glutamyl transpeptidase (GGT), antibody to Hepatitis A virus (HAVAb-IgG, HAVAb-IgM), hepatitis B surface antigen (HBsAg), lactate dehydrogenase (LD), neonatal bilirubin, prealbumin, total bilirubin, total protein, and the like.

Analytes related to pregnancy and fertility include, for example, human chorionic gonadotropin (hCG), beta-hCG, total beta-hCG, luteinizing hormone (LH), follicle stimulating hormone (FSH), dehydroepiandrosterone sulfate (DHEAS), estradiol, free estriol, total estriol, progesterone, prolactin, sex hormone binding globulin (SHBG), testosterone, and the like.

Analytes to determine blood disorders include, for example, B12, ferritin, folate, haptoglobin, and transferrin.

Analytes used to determine cardiac disorders include, for example, C-reactive protein (CRP), highly sensitive C-reactive protein (hsCRP), creatine kinase (CK), CK-MB, myoglobin, troponin, B-type natriuretic peptide (BNP), apolipoprotein A1, apolipoprotein B, and high density lipoprotein (HDL).

Cancer analytes include, for example, prostate specific antigen (PSA), free PSA, total PSA, fecal occult blood (FOB), acid phosphatase, alpha-fetoprotein (AFP), beta-2 microglobulin, CA 125™, CA 15-3™, CA 19-9™, carcinoembryonic antigen (CEA), PAP, pepsinogen, sqaumous cell carcinomas (SCC), and the like.

Analytes associated with inflammation and immunology include, for example, C3, C4, CRP, IgA, IgG, IgM, RF, and the like.

Analytes used to determine exposure to disease causative organisms include, for instance, rubella IgG, rubella IgM, toxoplasmosis IgG and IgM, cytomeglovirus (CMV) IgG and IgM, HTLV III, Anti-EBNA, mononucleosis, HAA, herpes, and anti-Streptolysin O.

Infectious disease analytes include microorganisms such as *Streptococcus pyogenes, Staphylococcus aureous* A, Endotoxin, Chlamydia, Syphillis, Gonococcus, *Helicobactor pylori* (*H. pylori*). Additionally, disease analytes include viral organisms such as hepatitis (HBV, HBsAg, HCV, HAA), hepatitis A virus, hepatitis B virus, hepatitis Non A-Non B, IgE, cytomeglovirus (CMV), herpes viruses, rubella viruses and the like. Further included, are, for example, toxoplasmosis, anti HTLV-I/HTLV-II, BSE, chagas antibody, CMV AB, CMV IgG, CMV IgM, CSF glucose, CSF protein, HIV AB, HIV-1/HIV-2 (rDNA), rotazyme II, and the like.

Analytes pertaining to endocrinology include, for example, thyroglobulin autoantibodies (anti-Tg), thyroid peroxidase autoantibodies (anti-TPO), C-Peptide, cortisol, HbA1c (hemoglobin fraction), PTH, triiodothyronine (T3), free T3, total T3, thyroid hormone, thyroxine (T4), free T4, total T4, thyroid stimulating hormone (TSH), and the like.

Pancreatic analytes include, for example, amylase, lipase, and the like.

Veterinary analytes include, for example, Heartworm Ag, *E. canis* Ab, Lyme Ab, *Giardia*, parvovirus, FIV, FeLV, and the like.

Analytes can also include, for example, insulin, gamma globins, allergens, cystic fibrosis antigens, toxins, such as those associated with tetanus and animal venoms, and insecticides.

The precise nature of a number of analytes together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which is hereby incorporated by reference in its entirety.

The signal provided to the user of the apparatus is provided by accumulation of a binding member such as a specific antibody and/or antigen; ligand and/or receptor ("binding molecule") conjugated to a label. In the instant embodiments, labels that produce a readily detectable signal are used. Thus, the instant embodiments provide colored labels which permit visible detection of the assay results without the addition of further substances and/or without the aid of instrumentation.

Examples of labels that can readily detected include, for example, dye sols, metal sols, nonmetal sols, colored latex particles, color indicators, colored matter encapsulated in liposomes, and the like.

Metal sols are disclosed in Leuvering, U.S. Pat. No. 4,313,734, issued Feb. 2, 1982 and Moeremans, et al., U.S. Pat. No. 4,775,636, issued Oct. 4, 1988, each of which is hereby incorporated by reference in its entirety, and comprise a metal, a metal compound, such as metal oxides, metal hydroxides and metal salts, or polymer nuclei coated with a metal or metal compound. The metal sols can comprise, for example, metals such as platinum, gold, silver and copper. Alternatively, or additionally, the metal sols can comprise metal compounds, such as, for example, silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide.

Nonmetal sols, such as carbon sols and their use are described in Kang, et al., U.S. Pat. No. 5,559,041, issued Sep. 24, 1996, which is hereby incorporated by reference in its entirety. Nonmetal colloidal particles, such as selenium particles, are disclosed in Yost, et al., U.S. Pat. No. 4,954,452, issued Sep. 4, 1990, which is hereby incorporated by reference in its entirety. Other nonmetals that can be used include elements within Group VIB. of the Periodic Table, such as sulfur, and tellurium.

Labels can also be formed from dye polymers, whereby dye molecules, or chromogenic monomers, are polymerized to form a colored polymer particle. Examples of such dyes include Congo red, Trypan blue, and Lissamine blue.

Organic polymer latex particles are disclosed in Tarcha, et al., U.S. Pat. No. 5,252,459, issued Oct. 12, 1993, which is hereby incorporated by reference in its entirety. Such particles can comprise a plurality of non-chromophoric monomers.

Particulate labels comprising a dye or other colored substance enclosed in liposome sacs are described in Campbell, et al., U.S. Pat. No. 4,703,017, issued Oct. 27, 1987; and Rosenstein, U.S. Pat. No. 5,591,645, issued Jan. 7, 1997, each of which is hereby incorporated by reference in its entirety.

The apparatuses described in these embodiments use test strips, dams and/or pads that can comprise a dry porous material. By "porous" it is meant that the matrix is composed of a material into which fluids can flow and can pass through. Representative materials include nylon, plastic, fiber containing paper, such as filter paper, chromatographic paper, and the like, nitrocellulose, glass fibers, polysullfone, polyvinylidene difluoride, polyurethane, and other porous polymers, polysaccharides, (e.g., cellulose materials, such as paper and cellulose acetate), silica, inorganic materials, such as deactivated alumina, diatomaceous earth, $MgSO_4$, or other inorganic finely divided material conveniently substantially uniformly dispersed in a porous polymer matrix, with polymers such as vinyl chloride, vinyl chloride-propylene copolymer, and vinyl chloride-vinyl acetate copolymer; cloth, both naturally occurring e.g., cotton and synthetic (e.g., nylon cloth), porous gels, (e.g., silica gel, agarose, dextran, and gelatin), polymeric films, (e.g., polyacrylamide), and the like. In exemplary embodiments, the test strips comprise POREX CHEMISTRY A and/or POREX CHEMISTRY K membranes commercially available from Porex Corporation, Fairburn, Ga., and/or NOVYLON brand membrane commercially available from Cuno Incorporated, Meriden, Conn.

The exemplary embodiments will be described in connection with the detection of HIV in a fluid specimen. Those skilled in the art will readily appreciate adaptation of these embodiments to detect other analytes indicative of other pathogens, or pathogenic conditions within body, food or environmental fluid samples.

Figure 1:
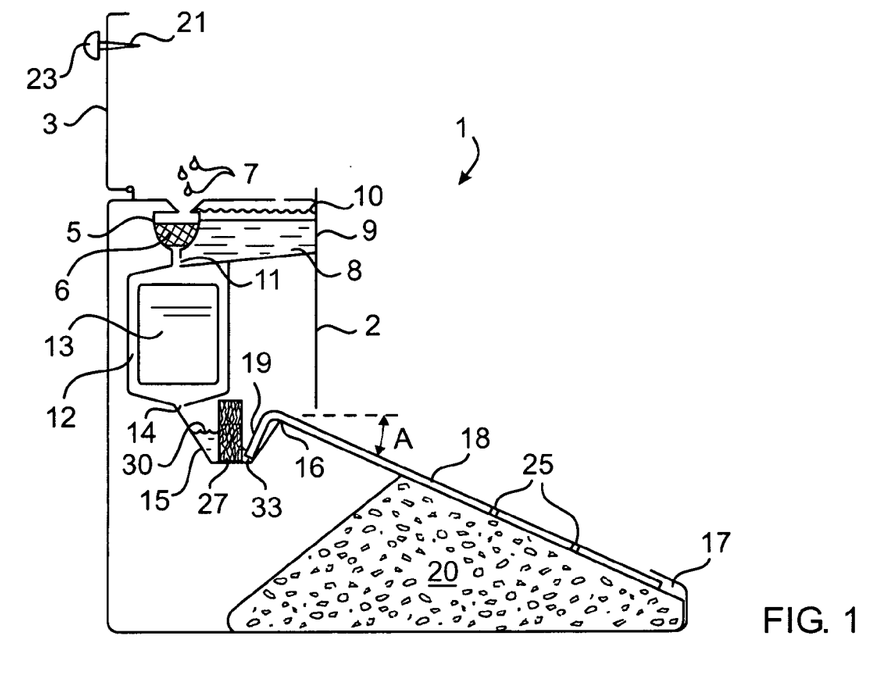
FIG. 1 is a diagrammatical cross-sectional illustration of a first embodiment of a interrupted flow testing apparatus.
Figure 2:
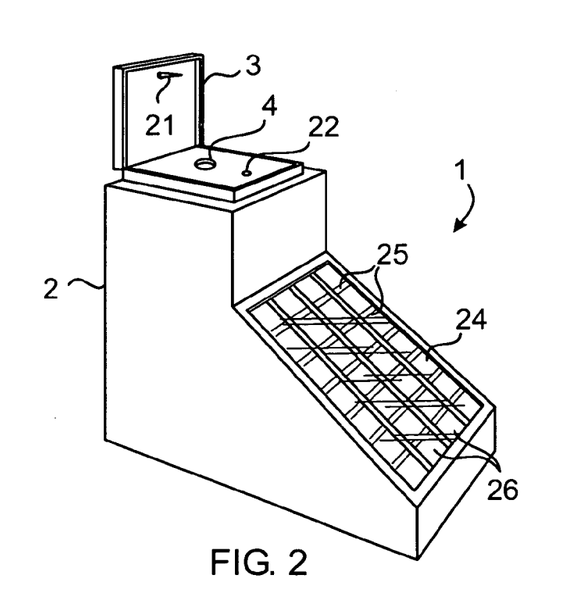
FIG. 2 is a diagrammatical perspective view of the apparatus of FIG. 1.

Referring now to the drawing, there is shown in FIGS. 1-2 a first example embodiment of an immunoassay testing apparatus 1 packaged in a molded plastic enclosure 2 topped by a sealing cap 3. In the upper region of the apparatus, and immediately under a ceiling hole 4 is a sampling well 5. The internal wall of the well is funnel-shaped, and retains some filtration material 6. The geometry of that wall, whether in the form of a V or a U, has a portion of a relatively low pitch so that when a drop, typically about 40 to 100 microliters, of fluid specimen 7 such as whole blood, or saliva runs along the wall, particles and adhesive matters are separated from the fluid component of the specimen. A supply of aqueous mix buffering solution 8 is held in a tank 9 along side the sampling well. In some embodiments, the mix buffer solution comprises Borax: 2-3%; nonfat dry milk: 0.2-0.5%; Sucrose: 0.05-0.1%; NaN3: 0.4%; Rabbit IgG: 2%; Goat IgG: 2%; Human IgG: 0.2%; Tween 20: 0.5% and the like.

The tank 9 has a top opening hermetically sealed by a membrane 10, and a dispensing port 11 in a lower region leading to a first chamber 12 in a first analytical part of the apparatus. The first chamber is located immediately below the sampling well and receives the fluid component and is subjectable to the buffering solution. The dispensing of the buffer solution 8 out of the tank 9 is triggered by puncturing the membrane 10. The puncturing is accomplished by a prong 21 which extends from the underside of the cap 3 and passes through an aperture 22 in the roof of the enclosure. The prong is normally held into a retracted position during storage and shipment of the apparatus, but can be moved to an extended position by manipulating a knob 23 on the outside of the cap. The prong is positioned, shaped and dimensioned to extend sufficiently through the aperture 22 into rupturing contact with the membrane 10. The buffer solution 8 combines with the fluid components of the specimen that come down from the sampling well to form a mixture which flows into the first chamber 12.

The first chamber 12 holds a conjugate pad 13 made of porous inorganic material such as fibreglass or 3M paper, and the like which has been coated with a soluble, lyophized amount of conjugate which includes at least one mobilizable binding member, specific to the analyte or analytes in question, conjugated to a visibly detectable label such as colloidal gold. In HIV testing, for example, the mobilizable binding member can include immuno-determinant epitopes of the HIV virus such as p18, p24, p32, gp36, gp41, p51, p55, p65, gp120, gp160 and subtype o. In this way the pad provides a source of labeled conjugate specific to the analyte or analytes in question. While the fluid mixture is exposed to the conjugate, an immuno-chemical reaction occurs wherein analytes in question from the specimen begin binding to the mobilizable binding members in the conjugate to form the first affinity binding labeled analyte complexes. It should be noted that alternately, the mix buffer solution can carry the an amount of conjugate in suspension. However, this can decrease the shelf life of the apparatus.

An outlet 14 at the bottom of the first chamber 12 leads to a pit 15 which forms a flow interrupting, incubation reservoir where the fluid 30 accumulates behind a porous dam 27 made of diffusive material whose function will be described in greater detail below. In general, the dam further mixes the fluid passing through it so that the fluid has greater chemical uniformity and is provided a temporary, but longer incubation time for the first affinity binding to reach a maximum.

Having passed through the porous, diffusive dam 27, the fluid accumulates in the downstream portion 33 of the pit until it flows over an escape port 16 leading to a second chamber 17 in a second analytical part of the apparatus which holds at least one chromatographic testing strip 18 oriented in an oblique, downward flow orientation, and which can be referred to as a "down-flow" strip. An upper edge 19 of the strip 18 extends into the downstream region 33 of the pit allowing the fluid to flow into and through the strip under the combined forces of gravity, siphoning and capillarity. The flow is enhanced by an absorbing pad 20 positioned in the bottom of the enclosure and in contact with a lower portion of the strip 18. The size of the absorbing pad is selected to accommodate the combined volume of the fluids within the apparatus. It should be understood that the diffusive, interrupting dam 27 is located between the conjugate source and the reaction membrane. In this way, there is no uninterrupted fluid flow contact between the conjugate source and the reaction membrane, but rather the fluid must pass through the diffusive dam before reaching any reaction membrane.

Each down-flow strip 18 can be positioned in an inclined position at a pitch angle A of at least 15 degrees from the horizontal. The down-flow strip differs from those common chromatographic strips typically used in lateral flow tests. The primary difference is that each down-flow strip does not provide a conjugate pad and is without a source of mobilizable labeled binding members, but does provide a reaction membrane having a number of test lines or zones 25 each coated with at least one immobilized capture binding member having an affinity for binding to the analyte or analytes in question. Immobilization techniques include reel to reel dispenser of binding members such as binding molecules. The down-flow test strips are then blocked to facilitate the test. Such a blocking procedure includes, for example, treating the strips with a buffer comprising Triton X-100: 1%; Polyvinyl Alcohol (PVA) (30,000-70,000 mw) or Polyvinyl Pyrrolidone (PVP) (10,000 mw): 1-1.5%; and Sugar: 0.2% and the like. It is important to note that by providing the conjugate and the reaction membrane in its constant, dried form, the apparatus can have a shelf life in excess of 2 years.

As the fluid passes through the membrane, a second immuno-chemical reaction occurs wherein the labeled analyte complex binds to the capture binding member to form the second affinity binding immuno-sandwich complex. The accumulation of the secondly bound immuno-sandwich complex beyond a threshold amount in the zone creates a colored test line. In this way the zones act as a test result signal generator. A transparent window 24 sealed to the enclosure provides a direct viewing of the test line zones 25 on a number of down-flow strips 26.

The reaction membrane region of the down-flow strip can be made from a single layer of substantially uniformly dispersed porous matrix material such as porous polyethylene commercially available from Porex Corporation of Fairburn, Ga. The substantially uniform dispersion of pores in the material reduces the negative effect of lot-to-lot variation present in prior membranes. This greater predictability in how a given strip will perform further enhances the sensitivity and accuracy of the test.

It should be noted that the buffer solution and fluid components of the specimen provide the volume of fluid necessary to fill the incubation reservoir and thus, regulate the transfer of the specimen through the apparatus. By adjusting the volume of buffer solution to what is necessary to create a minor and/or relatively slow overflow of the reservoir, excessive flooding and rapid flow through the strip is avoided. Further, it should be noted that the escape port 16 acts as a means for restricting the flow therethrough. It is further understood that the location, shape and capacity parameters of the pit 15 and the shape and dimension parameters of the dam 27 can be adjusted to provide a temporary, but longer incubation time, or better mixing of the mixture depending on its anticipated volume and viscosity.

Within about 0.5-2 minutes, the relatively slow speed of the flow of the mixture through the dam 27 and over the escape port 16 caused by the combination of siphoning, gravity and capillarity action forces, promotes a maximum degree of the second affinity binding on the down-flow strips. The two maximized affinity binding steps in turn maximize the diagnostic sensitivity of the RCIT apparatus technology.

Further, such sensitivity allows for the creation of a quantitative assay strip having a number of lines where each line is selected to appear at a different concentration threshold. In this way, the apparatus carrying one or more quantitative assay strips can provide the digital display of a quantitative result. Further, the apparatus can be adapted to include an electronic sensor for automatically detecting the result and an electronic display, such as a liquid crystal display (LCD) for displaying the results. Each of a plurality of strips can be coated with a number of corresponding antigenic epitopes (or polymers, proteins, polypeptides, etc.) which are immuno-determinant analytes for the pathogen in question, such as the HIV or the condition in question such as cancer. In HIV confirmatory detection, the appearance of at least two epitope lines on a down-flow strip will not only confirm the presence of HIV, but will also give a qualitative, analytical indication of the type of antibodies present in the specimen which can change during different periods of HIV infection and/or Acquired Immune Deficiency Syndrom (AIDS). Additionally, each strip can include a control line, working as an internal system control indicator. Therefore, any positive result of HIV detection shown by this RCIT method can include at least three (3) lines appearing in the test reaction window.

Referring now to FIGS. 3-7, the detailed operation of the interrupting, diffusive dam structure will now be described. The shape and dimensions of the pit 15, and the size and location of the dam 27 are further selected to avoid fluid flow over the top 31 of the dam. An example is selecting the elevation of the top of the dam to be a distance D above the elevation of the escape port 16.

Figure 3:
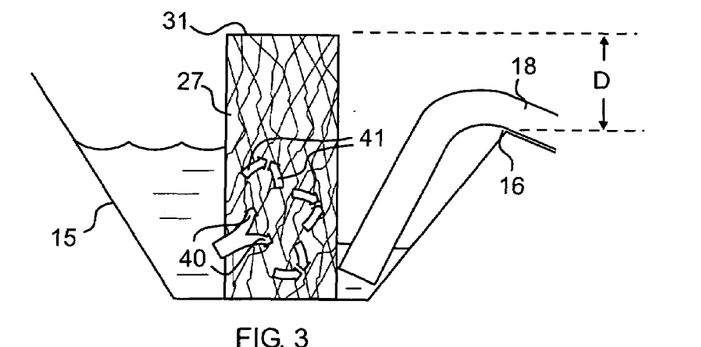
FIG. 3 is a diagrammatical cross-sectional side view of the apparatus of FIG. 1 showing the fluid flow through the dam.

The diffusive nature of the dam 27 causes the flow to separate at the fluid front into a plurality of branches or furcations 40 which, when these furcations converge and join together again, do so from different directions. The convergence from different directions 41 causes a mixing across the fluid front and hence the entire specimen as it flows through. This mixing can cause the break-up of clumps of non-analyte molecules which may carry mobilizable labeled binding members, and/or clumps of the analyte itself and/or clumps of labeled analyte complexes which could carry additional mobilizable labeled binding members. The breaking up of these clumps help the to reduce the possibility of a false positive result. The mixing also reduces the differences in the concentrations of non-analyte molecules and labeled analyte complexes so that they are spread more evenly. Once the fluid passes through the dam, the concentrations have superior uniformity which leads directly to giving the labeled analyte complexes a greater opportunity to form the second affinity binding and thereby helping to reduce the possibility of a false negative result.

In addition, the diffusive action of the porous dam 27 automatically further delays or interrupts the flow from the first chamber 12 to the reaction membrane of the down-flow strip 18 providing more incubation time for the first affinity binding to reach a maximum, thereby increasing the overall sensitivity and specificity of the test.

Figure 4:
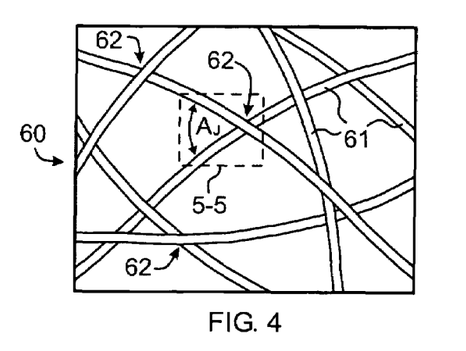
FIG. 4 is a diagrammatical microscopic illustration of fibers in a diffusive, flow interrupting pad material.

Referring now to FIG. 4, there is shown a portion 60 of a diffusive dam made from relatively non-reactive, porous material such as fiberglass, cellulose, polysullfone, NYLON brand material, polyethylene, NOVYLON brand material, POREX CHEMISTRY K brand material, POREX CHEMISTRY A brand material, FILTRONA brand material, and the like, all commercially available. The material is selected to have intersecting surface structures such as fibers 61 oriented substantially differently to one another to create a plurality of junctions 62 where there is typically an angle $A_j$ formed between the two intersecting structures at their junction where the angle is not 0 degrees. In other words, at the junction, the fibers should not be substantially parallel so that they provide intersecting surfaces which, through surface tension forces cause the fluid to branch into furcations and converge causing a more thorough intermixing. It is important to note that the viscosity of the fluid can be a factor in determining the optimum density of fibers and hence the number of junctions required in a given volume of material. It has been found that fiberglass material commercially available from JBC of Elyria, Ohio provides an adequate number of junctions for many applications. Other non-fibrous porous materials can also be used that provide intersecting surface structures to cause fluid furcation and intermixing, and provide the capability for carrying a dried surfactant.

Figure 5:
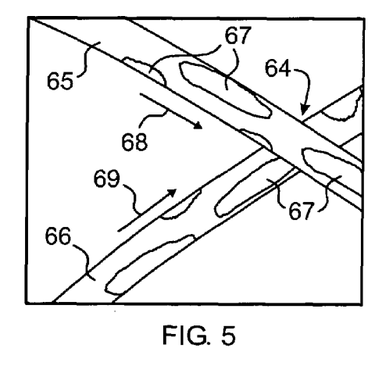
FIG. 5 is a diagrammatical microscopic close-up illustration of a fiber junction of a diffusive, flow interrupting pad material of FIG. 4 taken at box 5-5.
Figure 6:
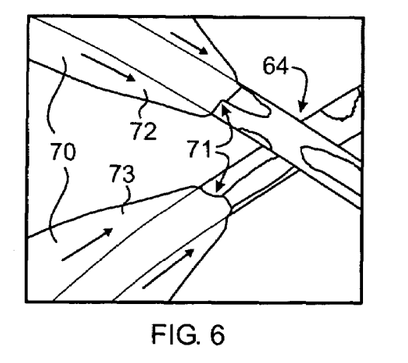
FIG. 6 is a diagrammatical microscopic illustration of the fiber junction of FIG. 5 where microscopic fluid flows are converging.
Figure 7:
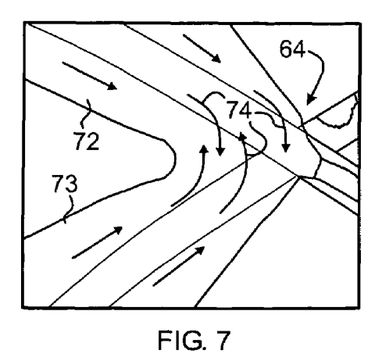
FIG. 7 is a diagrammatical microscopic illustration of the fiber junction of FIG. 5 where microscopic fluid flows have converged and mixed.

The portion of the diffusive dam can be pretreated with a surfactant by immersing the dam material during manufacturing into an amount of liquid surfactant so that it penetrates substantially all of the pores of the dam material. The dam material is then dried. This leaves a residue of the surfactant on the intersecting surface structures. As shown in FIG. 5, the junction 64 of two intersecting surface structures such as fibers 65,66 having dried surfactant residue 67 thereon creates two convergent fluid paths 68,69. As shown in FIG. 6, fluid 70 flowing through the dam will at its fluid front 71 have an affinity for separating into branches or furcations 72,73 which each tend to flow along the fluid paths formed by each surfactant treated fiber. As shown in FIG. 7, the furcations 72,73 will meet at the fiber junction 64 and their respective velocities will cause an intermixing as indicated by flow lines 74.

An exemplary surfactant is a detergent such as polyethylene glycol sorbitan monolaurate commercially available under the brand name TWEEN 20 from Sigma-Aldrich Corporation of St. Louis, Mo. Other detergents are acceptable such as TRITON X-100 brand, TRITON X-114 brand, TWEEN 80 brand, and sodium dodecyl sulfate ("SDS") detergents also available from Sigma-Aldrich Corporation. Depending on the test being conducted, other anionic, cationic, non-ionic and Zwitterionic detergents may also be acceptable.

Figure 8:
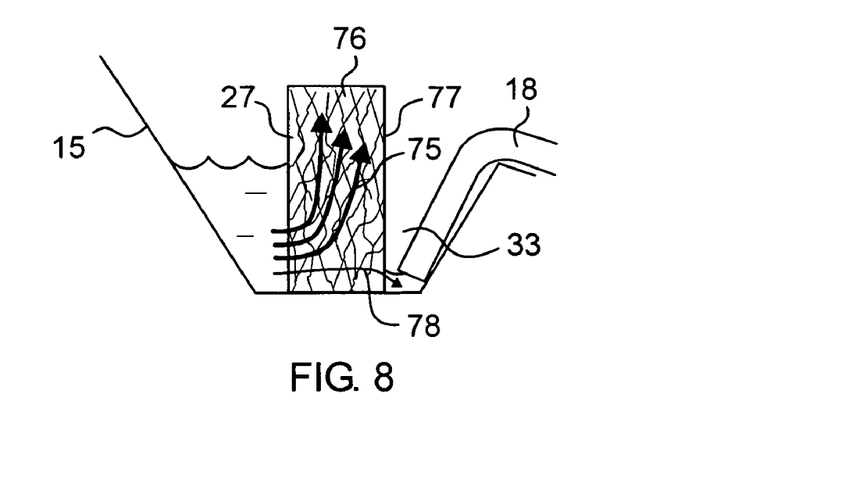
FIG. 8 is a diagrammatical cross-sectional side view of the apparatus of FIG. 1 showing the initial fluid flow into a dry dam.

Referring now to FIG. 8, the fluid flow being driven primarily through capillary forces will tend toward fully saturating the diffusive dam 27 before any substantial flow exits the dam. This preferential fluid flow direction is primarily due to the differential surface tension caused by the surfactant treatment of the surface structures in the dam. Arrows 75 indicate that the predominant flow will be first toward the dry top portion 76 of the dam rather than out of the downstream side 77 of the dam and into the downstream region 33 of the pit 15 as indicted by the smaller flow arrow 78. In this way the dam acts partially as a reservoir for delaying or interrupting the flow giving more time for first affinity binding to occur. Depending on the chemistry of the test being performed and the viscosity of the sample being tested, the flow can be delayed between about 1 and about 40 seconds. For relatively low viscosity samples such as urine, the flow can be delayed for between about 2 and about 3 seconds.

Figure 9:
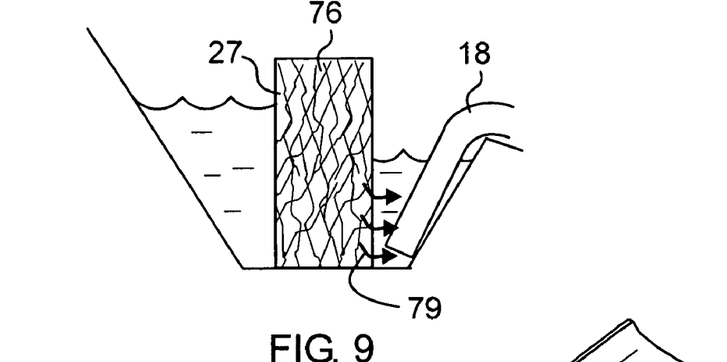
FIG. 9 is a diagrammatical cross-sectional side view of the apparatus of FIG. 1 showing the fluid flow out of a saturated dam.

Referring now to FIG. 9, as the dam 27 eventually becomes saturated, the fluid pressure, due to continued capillary action and gravity, builds at the downstream side until the flow begins to exit 79. This relatively rapid breakdown of the surface tension barrier at the downstream side causes further mixing and leads to a more evenly mixed exiting fluid front. Further, because of the vertical structure of the diffusive dam 27, the initial fluid front generally stagnates at the top portion 76 of the dam while the fluid front exiting the dam is fluid from the more predictably mixed, non-initial-front fluids at the bottom of the dam. In this way, the surfactant treated dam provides an additional, initial fluid front bypass function which increases uniformity of the first amount of fluid reaching the reaction membrane, which enhances the sensitivity and specificity of the affinity bindings described above.

Pretreatment of the dam can also be in the form of pH conditioning chemicals, and non-specific adhesive blocking molecules which will selectively filter or "block-out" unwanted non-analyte adhesion molecules, typically proteins, which can non-specifically interfere and/or compete with the analyte in question in either or both of the first and second affinity binding stages of the test.

Figure 10:
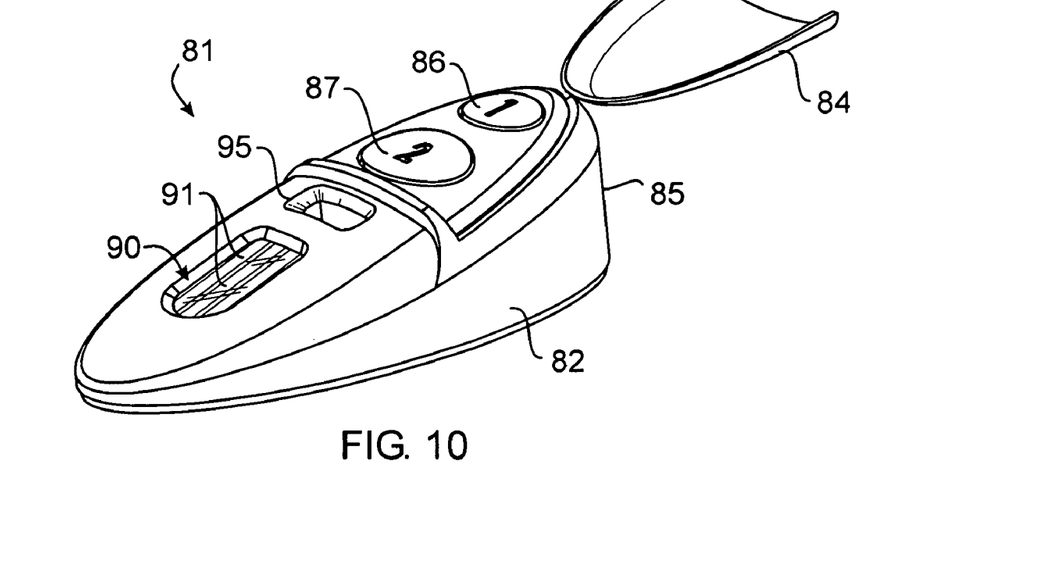
FIG. 10 is a perspective view of an alternate embodiment of the interrupted, diffusive downward flow testing apparatus having programmed dispensing of mix and wash buffers.
Figure 11:
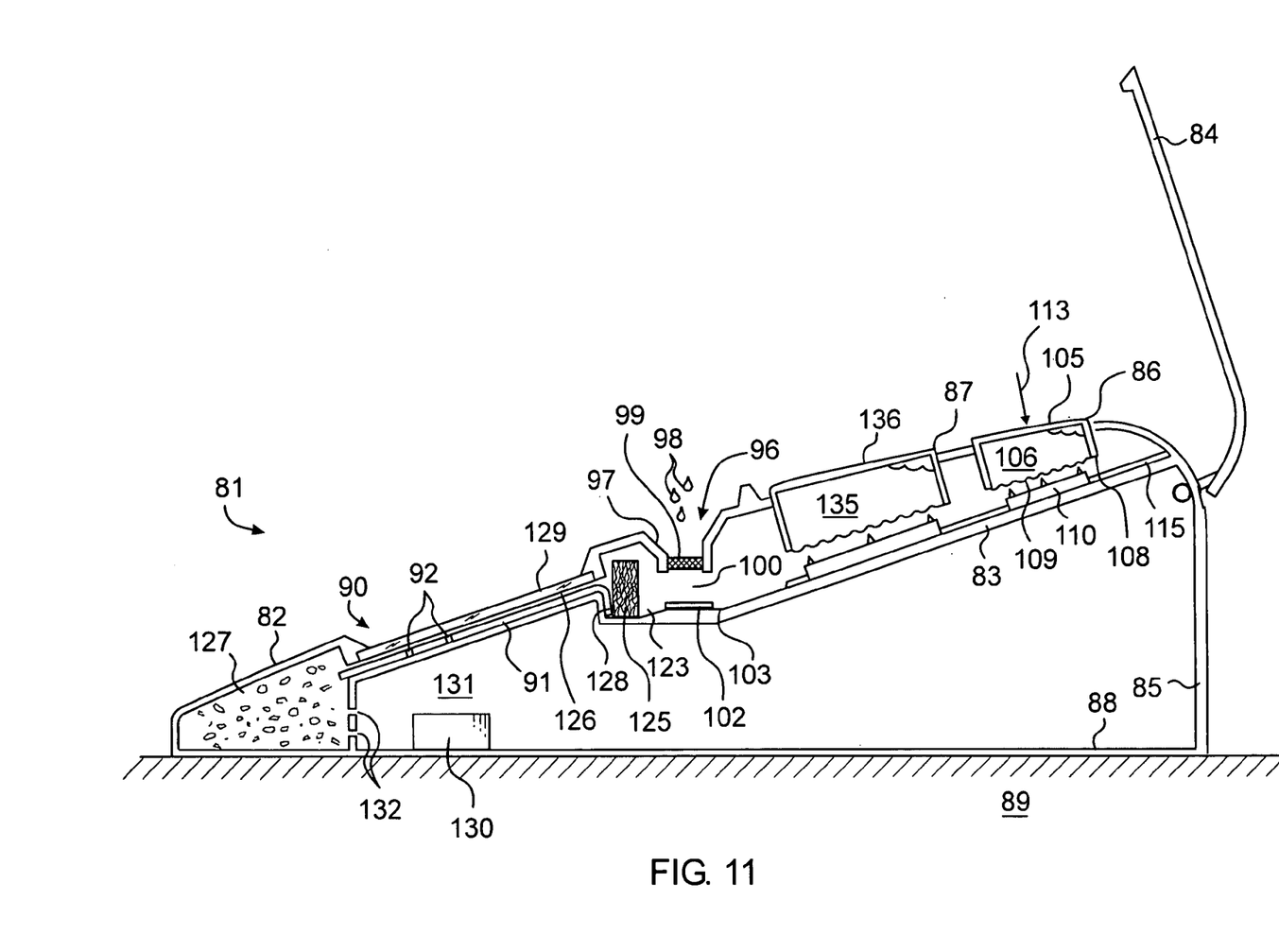
FIG. 11 is a diagrammatical cross-sectional side view of the apparatus of FIG. 10.
Figure 12:
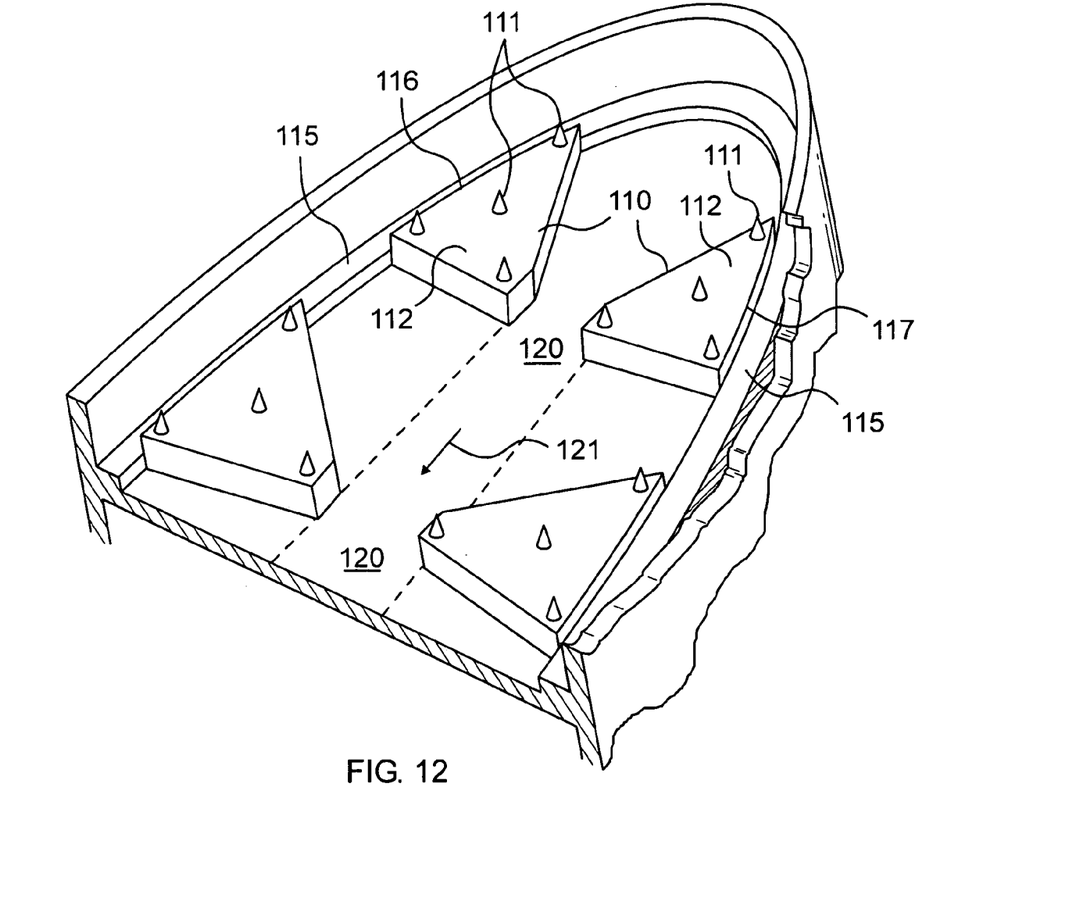
FIG. 12 is a diagrammatical perspective view of the tank fracturing pedestals of the apparatus of FIG. 10.

Referring now to FIGS. 10-12, there is shown a further embodiment of an immunoassay testing apparatus 81. The apparatus is packaged in a molded plastic enclosure 82 having an internal base pan 83. A retractable protective cover 84 is hingedly mounted at the back end 85 of the enclosure. The cover is in a closed position during storage and shipment of the apparatus to protect a pair of operation buttons 86,87 from being inadvertently pressed, but can be flipped open for testing. The enclosure is shaped to have. a generally planar bottom support surface 88 to support the apparatus upon a level surface 89 so that a test station 90 holding one or more down-flow testing strips 91, having test line zones 92, is oriented in an inclined position from the horizontal.

In the medial region of the apparatus, and immediately under a ceiling hole 95 is a sampling well 96 having a funnel-shaped internal wall 97 and a filter screen 99 to help separate particles and adhesive matters from the fluid component of a specimen 98 such as whole blood or saliva. The sampling well 96 leads downwardly to a first, premix chamber 100 which receives the fluid component of the specimen in a first analytical part of the apparatus. The specimen drops upon a conjugate pad 102 located on the floor 103 of the premix chamber thereby exposing the specimen to a source of conjugate. The viscosity of blood or saliva for example generally prevents it from flowing on its own through to the rest of the apparatus. The shape and dimensions of the first chamber can be adapted for other different viscosity fluid specimens.

The analytical testing reaction is initiated by opening a first tank 105 containing a measured amount of mix buffer solution 106. The tank is formed by a generally inverted cup-like button structure 86 made from a durable, rigid, fluid impermeable material such as hard plastic. The cup structure rim 108 is breakably thermo-sealed by a foil-plastic membrane 109. In its pretest position the mix buffer tank rests above a pair of puncturing pedestals 110 each having a plurality of prongs 111 extending upwardly from the pedestal upper surface 112. The prongs are located near the periphery of each pedestal to help cause fracturing of a pliable foil-plastic membrane. The tank is opened by downward pushing manipulation 113 of the first button 86 which causes the tank to be lowered onto the pedestals, fracturing the foil-plastic membrane. Downward motion is stopped by a peripheral lip 115 straddling the outer lateral edges 116,117 of the pedestals. The pedestals are laterally spaced apart to form a fluid channel 120 therebetween allowing the solution to flow out of the tank and down 121 toward the premix chamber 100.

The mix buffer solution 106 is dispensed into the premix chamber 100 to contact the conjugate pad 102 and mix with the specimen to form a fluid mixture and initiate the first affinity binding reactions. In this way the premix chamber is subjectable to the mix buffer solution which can be characterized as a reactive solution. The button and openable tank forms a built-in manipulable member for triggering the dispensing of the mix buffer solution onto the specimen. The amount or volume of mix buffer solution 106 is selected to adequately react with the amount of specimen. In this embodiment the volume of mix buffer is between about 200 and 300 microliters, and can be about 250 microliters.

Similarly to the previous embodiment, the mixture collects in a pit 123 formed into the floor 103 of the premix chamber 100. The pit is shaped and dimensioned to have a given capacity to form a temporary incubation reservoir behind a porous dam 125. The mixture flows slowly and diffusively under the combined effect of gravity, capillarity, and siphoning forces through the dam and into one or more down-flow testing strips 91 held in a second chamber 126 in the test station 90 and eventual on to a flow absorbing pad 127 contacting the lower edge of the strips. The upper edge 128 of the strips extend into the pit 123 and contact the downstream side of the dam 125. A transparent window 129 sealed to the enclosure provides for direct viewing of the strips 91. A block of desiccant 130 is held in a third chamber 131 in the enclosure and is in communication with the absorbing pad through holes 132 to help extend shelf life. Additionally, another embodiment provides that the entire apparatus is kept in a sealed hermetic aluminum plastic foil pouch bag until use.

The apparatus also provides for a supply of a stop wash buffer solution 135 to the down-flow strips in order to stop the reaction in the strips and to carry away lingering chemicals and residue which could serve to obscure the lines formed in the zones 92 on the strips 91 and also to remove any other non-specific materials from the reaction area. For example, one such stop wash buffer comprises: Tween 20: 1%; Glycerol: 0.5%; Glycine: 5-20 mM; and NaN3: 0.02% and the like.

The stop wash buffer solution 135 is contained in a second tank 136 located upstream from the premix chamber 100 and which is openable in a manner similar to the mix buffer tank 105 thereby providing a built-in, manipulable member for releasing the wash solution onto the down-flow strips.

The wash buffer can be applied after a certain programmed-waiting period which allows for the mixture to be drawn through the strips to an adequate degree. The waiting time can of course be dependent on the type of test being performed. For HIV detection the waiting period can be between about 0.5 and 2 minutes. The amount of wash buffer solution is selected to adequately wash the down-flow strips without unduly increasing the bulk of the apparatus, and in this embodiment is between about 2 and 3 milliliters, and can be about 2.5 milliliters. In this embodiment the volume of wash buffer is about ten times that of the mix buffer. The flow of the stop wash buffer occurs relatively more quickly than the first flow of the mixture. The wash buffer, having about ten times the volume of the mixture, rapidly penetrates the already moistened dam and flushes out the non-specific binding caused by non-specific materials in the reaction area. This action helps to maximize the specificity of the present apparatus to provide RCIT.

It is understood that both of the tanks 105,136 are in fluid flow communication with the channel 120 which is in fluid flow contact with the premix chamber 100 which is in fluid flow contact with the dam 125 which is in fluid flow contact with the strips 91, meaning there is a fluid path from the tanks, through the premix chamber 100, to the test station 90.

Figure 13:
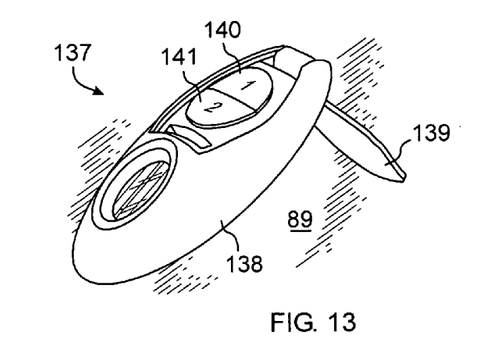
FIG. 13 is a diagrammatical perspective view of a further alternate embodiment of the interrupted, diffusive downward flow testing apparatus having a spring loaded cover/support leg and more than one diffusive dam.
Figure 14:
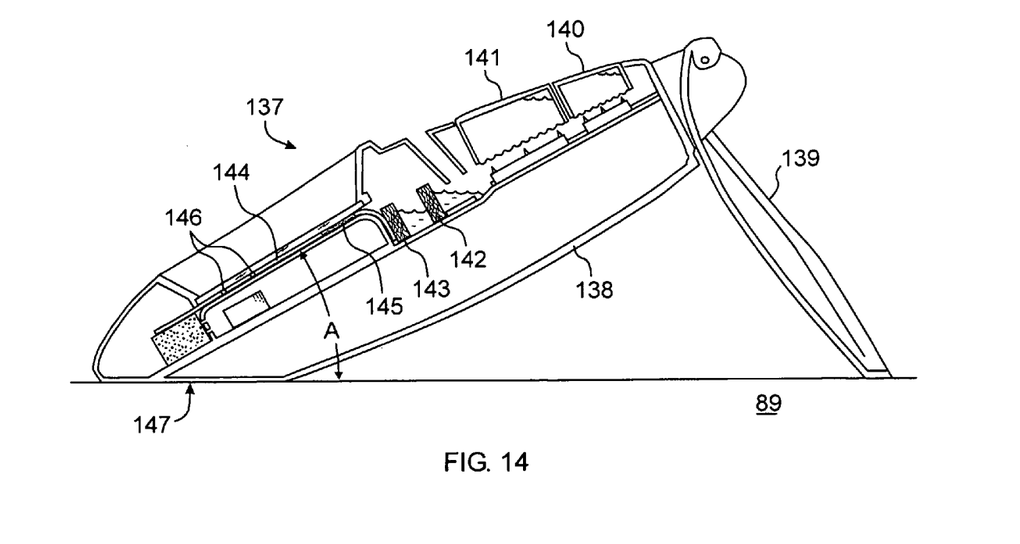
FIG. 14 is a diagrammatical cross-sectional side view of the apparatus of FIG. 13.

Referring now to FIGS. 13 and 14, there is shown another alternate embodiment of an immunoassay testing apparatus 137 which operates similarly to the previous embodiment. The apparatus is packaged in a compact and rounded molded plastic enclosure 138 and includes a spring-loaded retractable protective cover 139 hingedly mounted at the back end of the enclosure. The cover is in a closed position during storage and shipment to protect a pair of operation buttons 140,141, but is flipped open position for testing. In this embodiment the cover swings nearly 270 degrees around so that it forms a support leg 139 in the open position to orient the apparatus at a favorably inclined angle A upon a level surface 89. The housing also has a flattened underside outer surface portion 147 at the opposite, front end of the enclosure to provide greater stability.

This embodiment is further characterized by two, diffusive porous dam structures 142, 143 spaced a distance apart from one another. In this way, the upstream diffusive dam 142 can have a different pretreatment condition than the downstream diffusive dam 143. For example, the upstream dam can be pretreated to have a pH conditioner; and the downstream dam be pretreated to have a non-specific adhesive blocking molecule and a surfactant.

By splitting the pretreatment chemicals between two or more dams, the test apparatus designer is not only given increased accuracy, but also more control and predictability over the reactions occurring at various stages of the testing process. Also, the designer is given the flexibility in assembly to inexpensively use the same housing design for a number of different tests depending on the type of dams, their pretreatment, the type of strips, the type of conjugate pad and buffer solutions which can easily be swapped. Also, using two or more pretreated dams potentially avoids manufacturing inconsistencies such as the second pretreatment chemical dislodging some of the first pretreatment chemical on a single dam.

It should be noted that in the multi-diffusive dam embodiments, no pretreatment can be a pretreatment condition. For example, the upstream dam 142 may simply be a fiberglass filter without any surfactant, pH conditioner or non-specific adhesive blocking molecule. In this case its pretreatment condition would be "unpretreated". This pretreatment condition would be different from the pretreatment condition of the downstream dam 143 which could have a dried surfactant pretreatment condition.

This embodiment shows that the down-flow strips 144 can be further adapted to have a pad 145 made from diffusive material to further mix the fluid as it flows down the strip. The diffusive pad is located upstream from the signal generating zones 146 carrying the immobilized binding members. Further, the pad may be pretreated similarly to the dams described above.

Again it should be noted that the increased accuracy provides the ability to make multi-line strips for detecting different analytes in a single specimen such as for detecting multiple major epitopes, i.e., antigenic determinants of an endogenious disorder such as AMI, or a single exogenous pathogen, or pathogenic organism such as bacteria, viruses such as HIV, parasites, rickettsia, and the like.

Referring now to FIGS. 15-20, there are shown alternate embodiments of the openable mix and wash buffer tanks. These embodiments provide means for dispensing the volume of solution from the tanks in a manner which is substantially uniform across a manufacturing run of many test apparatuses, while keeping the apparatus inexpensive to manufacture, and making the tanks resistant to inadvertent opening.

Figure 15:
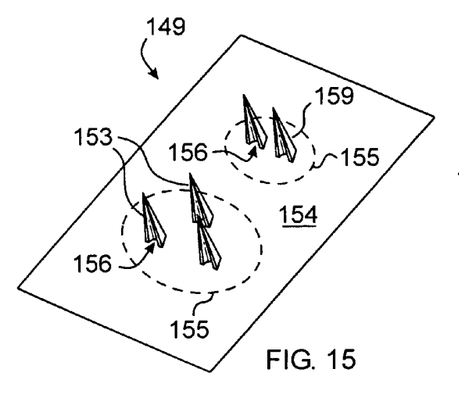
FIG. 15 is a perspective view of an alternate embodiment of the mix and wash buffer dispensing means having a puncturable bladder.
Figure 16:
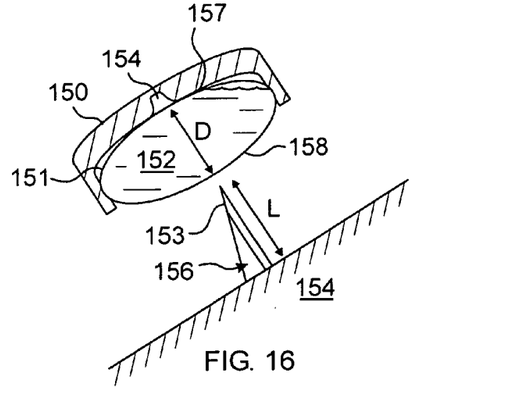
FIG. 16 is a diagrammatical cross-sectional side view of the dispensing means for FIG. 15.

As shown in FIGS. 15-16, there is a first example of an opening structure 149 where the tanks are each formed by an inverted hollow cup-like button structure 150 adapted to hold a hermetically thermo-sealed bladder 151 containing either the mix or wash buffer solution 152. The tank is opened by pushing it down upon one or more prongs 153 extend upwardly from the base pan 154 of the apparatus under the footprint 155 of each of the tanks. Each prong is shaped to have an axial groove 156 which acts as an air channel to encourage the evacuation of the bladder 153 when it is punctured. Further, the length L of the prongs is selected to be greater than the distance D between the opposite top and bottom walls 157,158 of the bladder so that the prongs puncture both opposite walls causing the wash buffer to flow more rapidly out of the bladder which ensures rapid washing of the down-flow strips at the preselected appropriate time. The button has recess 154 in the form of an air conduit sized to accommodate the insertion of the tip of the prong and to thereby facilitate evacuation of the bladder. Each prong is also shaped to have an upstream oriented convex prow 159 to prevent collection of buffer solution behind the prong.

Figure 17:
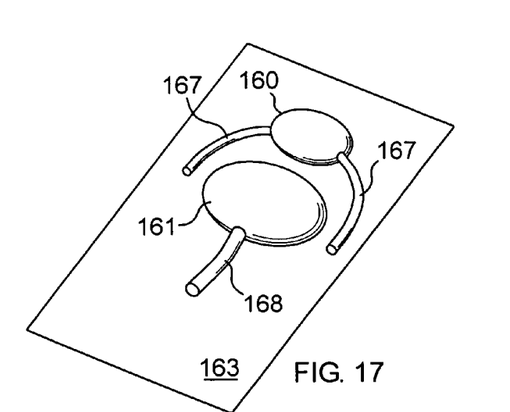
FIG. 17 is a perspective view of another alternate embodiment of the mix and wash buffer dispensing means having crushable bladders having discharge tubes.
Figure 18:
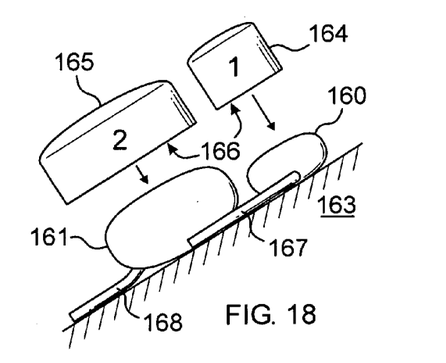
FIG. 18 is a diagrammatical side view of the dispensing means for FIG. 17.

FIGS. 17-18 show an alternate embodiment of an opening structure where the mix tank 160 and wash tank 161 are formed by a pair of bladders secured atop the base pan 163. Each bladder is opened by being crushed by a respective button 164,165. Each button has a substantially flat lower surface 166 that moves toward the base pan during the opening process. The mix buffer tank 160 has a pair of discharge tubes 167 running down the base pan on either side of the wash buffer tank 161 so that the mix buffer is not trapped behind the wash buffer tank. The wash buffer tank 161 has a least one discharge tube 168 running down the center of the base pan. The use of discharge tubes allows for a more predictable dispensing of the buffer from the respective tank. Otherwise the tank may rupture in an unpredictable way sending buffer in an unintended direction to be trapped.

Figure 19:
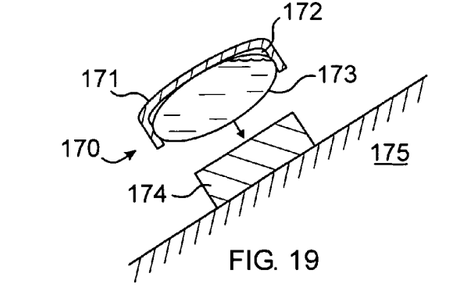
FIG. 19 is a diagrammatical cross-sectional side view of yet another alternate embodiment of the mix and wash buffer dispensing means having a bladder crushable over an intimately engaging pedestal.
Figure 20:
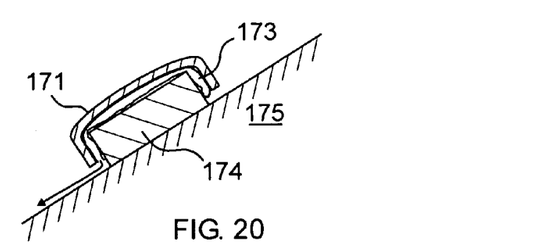
FIG. 20 is a diagrammatical side view of the dispensing means for FIG. 19 in an open, crushed condition.

FIGS. 19-20 show an alternate embodiment of an opening structure where the respective tank 170 is formed by an inverted, cup-like button structure 171 having a cavity 172 carrying a bladder 173 similarly to the embodiment of FIGS. 15-16. However, in this embodiment the frangible bladder 173 is opened by being crushed over a pedestal 174 extending upwardly from the base pan 175 and sized and shaped to intimately engage the cavity 172 thereby more completely crushing the bladder and forcing the buffer solution out.

The interrupted, diffused, down-flow test can rapidly provide an analytical panel or profile of antigen or antibody detection, and confirm the biochemical or pathogenic condition such as HIV infection, or early stage cancer prior to metastasis, or acute cardiac disorder by way of a simple, inexpensive and disposable apparatus that can be manipulated safely by a relatively low skilled person. The quality of the clinical performance of this novel platform technology surpasses previous rapid testing technologies, such as Latex particle agglutination, Flow-Through test, and the currently wide-spread Lateral Flow apparatuses. It is a technology of Rapid Confirmatory Immunological Testing (RCIT).

While the exemplary embodiments have been described, modifications can be made and other embodiments may be devised without departing from the spirit of the invention and the scope of the appended claims.

What is claimed is:

1. A flow immunoassay testing apparatus for testing a fluid specimen for the presence of an analyte, said apparatus comprises:
    a first chamber shaped and dimensioned to accept said specimen and be subjectable to a supply of mix buffer solution and a source of labeled conjugate specific to said analyte;
    a second chamber holding at least one test result signal generator responsive to an amount of said analyte bonded to said labeled conjugate;
    a first mixing dam located on a fluid path between said first and second chambers;
    said dam comprising a diffusing, porous first material having fibers oriented substantially differently to one another, and branching into furcations and convergences; and
    a flow interrupting reservoir comprising a pit separated into a first region and a downstream region by said first dam.

2. The apparatus of claim 1, wherein said first material has a first pretreatment condition.

3. The apparatus of claim 2, wherein said first pretreatment condition is selected from the group consisting of: being pretreated with a surfactant; being pretreated with a pH conditioner, being pretreated with a non-specific adhesive blocking molecule; and, having no pretreatment.

4. The apparatus of claim 3, wherein said surfactant comprises a non-ionic detergent.

5. The apparatus of claim 1, which further comprises a second dam spaced a distance apart from said first dam in said downstream region, wherein said second dam comprises a second diffusive, porous material substantially similar to said first material.

6. The apparatus of claim 5, wherein said second material has a second pretreatment condition, and said first pretreatment condition is different from said second pretreatment condition.

7. The apparatus of claim 1, wherein said first material is selected from the group consisting essentially of: cellulose, polysullfone and fibrous plastic.

8. The apparatus of claim 1, wherein said generator comprises a chromatographic test strip including a zone held on a membrane in an oblique, downward flow orientation.

9. The apparatus of claim 8, wherein said membrane comprises a plurality of test zones adapted to provide a measurable basis for a quantitative result display.

10. The apparatus of claim 8, wherein said membrane comprises a plurality of test zones adapted to provide a measurable basis for a qualitative result display.

11. The apparatus of claim 8, wherein said strip is formed without a source of mobilizable labeled binding members.

12. The apparatus of claim 8, wherein said strip further comprises a diffusive pad upstream from said zone.

13. The apparatus of claim 1, wherein said second chamber comprises a plurality of chromatographic test strips adapted to provide a measurable basis for a quantitative result display.

14. The apparatus of claim 1, wherein said signal generator is adapted to provide a measurable basis for a quantitative result display.

15. The apparatus of claim 14, wherein said conjugate source comprises a lyophilized amount carried on a structure within said first chamber.

16. The apparatus of claim 14, wherein said mix buffer solution is preformulated to carry an amount of said conjugate source in suspension.

17. The apparatus of claim 1, which further comprises means for triggering a dispensing of said supply into said first chamber.

18. The apparatus of claim 1, wherein a volume of said supply of mix buffer solution is adjusted to create a minor outflow through said dam.

19. The apparatus of claim 1, which further comprises an openable tank shaped and dimensioned to releasably hold an amount of a wash buffer, wherein said tank in an open condition is in fluid communication with said dam.

20. The apparatus of claim 1, wherein said supply of mix buffer solution has a volume between about 200 microliters and about 300 microliters.

21. The apparatus of claim 1, which further comprises a supply of wash buffer solution having a volume between about 2.5 milliliters and about 3 milliliters.

* * * * *